United States Patent [19]
Potocki

[11] Patent Number: 5,169,319
[45] Date of Patent: Dec. 8, 1992

[54] METHOD FOR IMPROVING A PERSON'S SKILL FOR PLAYING AN INTERACTIVE VIDEO GAME REQUIRING EYE-HAND COORDINATION AND OPERATION OF MANUAL ACTIVATION MEANS

[76] Inventor: John Potocki, 723 Johnston Ave., Trenton, N.J. 08629

[21] Appl. No.: 559,849

[22] Filed: Jul. 30, 1990

[51] Int. Cl.$^5$ .............................................. A63F 9/00
[52] U.S. Cl. .................... 434/236; 434/237; 434/238
[58] Field of Search ............... 434/236-238, 434/307-318; 273/DIG. 2.8, 436, 856, 434

[56] References Cited
U.S. PATENT DOCUMENTS
4,342,454 8/1982 Baer et al. ................ 273/85 G
4,586,905 5/1986 Groff .......................... 434/308 X OTHER PUBLICATIONS
Juliani, Review of Jack Nicklaus Greatest 18 Holes of Championship Golf Oct. 3, 1989, pp. 1-2.
Norman, Par for the Course, Aug. 1989, pp. 2-5.
Howell, Ace Amusement Mach., Drawing, Jul. 81, Playmeter p. 43.

*Primary Examiner*—Richard J. Apley
*Assistant Examiner*—Glenn E. Richman
*Attorney, Agent, or Firm*—Abdallah & Muckelroy

[57] ABSTRACT

A method for improving a person's skill in playing a known one player adventure video game in which a television screen is used to display a video tape of a player or computer, for example, playing through all levels of the video game. By stress reduction associated with teaching escapes, the person's skill for playing the video game increases dramatically especially upon playing the game immediately after having observed a player playing the game through all levels of play. Subliminal and/or audio messages on the video tape describing what actions are being taken by the player at each level of play of the video game further increases a person's skill for playing the video game.

2 Claims, 3 Drawing Sheets

METHOD FOR IMPROVING A PERSON'S SKILL FOR PLAYING AN INTERACTIVE VIDEO GAME REQUIRING EYE-HAND COORDINATION AND OPERATION OF MANUAL ACTIVATION MEANS

BACKGROUND OF THE INVENTION

1. Field of the Invention

This invention relates to the field of interactive single player video games wherein the game comprises computer generated images from an electronic device displayed on a television monitor. More specifically, the invention concerns an amusement and information system which uses a form of learning feedback, subliminal messages, stress reduction and knowledge developed during play of the game to facilitate rapid learning of new eye-hand combinations and new ways of operating the manual activation means necessary to more effectively interact with the video game and play it. 2. Description of the Prior Art U.S. Pat. No. 4,028,773 to Ulicki discusses a system for providing a video display of a pictorial information message on a video display device. U.S. Pat. No. 4,584,603 issued in 1986 to Harrison discloses an amusement and information system for use in a passenger carrier. U.S. Pat. No. 4,192,510 was issued in 1980 to Miller for an apparatus simulating the game of golf. The actual drives and approach to the green are played on a practice driving range image generated by a computer. The golfer plays realistically any recorded courses and measures his game against the par for those courses via the game processor, completely putting out for a final score on a computer practice green.

In 1988 U.S. Pat. No. 4,774,679 was issued to Carlin for a stride evaluation system. This patent disclosed a system for displaying the current magnitude of stride forces produced by a sport participant in a sporting event having a first portable housing placed on the legs of the participant for sensing the stride force and a second portable housing located elsewhere on the body of the participant for receiving the force signals from each portable sensor located on the legs of the participant and for storing that information by transmitting it to a remote location.

In 1989 U.S. Pat. No. 4,844,476 was issued to Becker for a video target response apparatus and method of employing a standard video tape player and television receiver. Becker discloses the use of the substantially unmodified standard video cassette player to play a tape on a similarly unmodified television receiver to display a scene, particularly including selected targets. Becker's system includes a learning mechanism, that is, a provision for analyzing the output to detect the presence of a pulse sequence associated with the target and for communicating the result of this analysis to the user.

Becker pointed out that video games and learning systems use input responses from either a keyboard or a joy stick. Becker indicates that some are based on the concept of aiming a gun and directed his invention primarily to aiming type games. In these games the computer and through it the computer monitor or television receiver receives signals from the gun and these signals are used to determine the accuracy of the aim thus providing the player some feedback regardig his play of the game. The results from the accuracy indications are used interactively by the program computer to generate display effects on the screen indicating where the gun was in fact pointed and in some cases also changes the screen display when the gun was aimed correctly. Further, scores are developed by the computer and fed back to the monitor or receiver screen for display along with the target display.

U.S. Pat. No. 4,662,635 issued in 1987 to Enokian discloses a multiple player video game and learning system. Enokian provides a video game in which actual plays or perfomances of living beings are displayed on a cathode ray tube in accordance with plays selected by at least two players of the video game. The invention includes record keeping apparatus to record the progress of each player toward a goal or score as indicated by each play selected. Enokian is directed to types of athletic contests and games such as football, baseball, hockey, basketball, soccer, tennis, volleyball, badminton, cricket and the like. The primary requirement being that the game has at least two opposing sides and each side has one or more players which distinguishes from the applicant's novel invention.

In 1979 U.S. Pat. No. 4,156,928 was issued to Inose et al for a programmable television game and training system with adaptable operator control. This invention provided a microprocessor based television game or training system to facilitate the user entering or devising his own programs and providing the user the ability to adapt the user controls of the system to the game or training sequence entered.

It is important to an understanding of the novel invention to recognize that stress and the negative effects of stress on the player plays a significant role in inhibiting a player from achieving additional levels of successful play. The playing of one player video games, repeatedly achieving a defeat level, makes the player undergo adrenalin surges. Sensitivity to adrenalin surges is a major factor in creating psychological stress associated with repeated play and inability to achieve a next play level, i.e., stress attributed to repeated defeat with no clear means to succeed to a higher level.

New studies in animals and humans suggest that specific sites in the brain undergo changes as a result of repetitive adrenalin surges.

Brain changes occur, scientists now indicate, when the stress is experienced as an overwhelming threat or one over which a person has no control as to the outcome. A game player repeatedly attempting to achieve a higher level of play in a game and being unable to do so experiences an uncontrollable stress which has a biological impact: diminution of coordination.

Evidence for biological changes in the brain as a result of stress has grown over the last ten years from laboratory experiments on animals who were subjected to stress, often electric shocks they could not escape, while their brain activity was studied. The main changes observed have been in the way in which the brain secretes chemicals it produces under stress. The effects seen in animals have recently been indirectly confirmed as also occuring in people. The changes occur in three ways:

(1) Some of the main changes are in the locus ceruleus, a structure which regulates the brain's secretion of two catecholamines, hormones that mobilize the body for an emergency. This structure becomes hyperreactive during play of a video game secreting the brain's chemicals especially in situations wherein the player identifies with the protagonist in the video game who is constantly threatened during the game.

(2) There are also increases in the secretion of corticothopin-releasing factor or CRF, one of the main hormones that mobilizes the body's reflexes to meet an emergency. This hormone is regulated by the circuit linking hypothalamus, a structure in the brain's emotional center and the pituitary gland. Increased secretions alert the body for emergencies perceive by the game player.

(3) The opiod system of the brain which can blunt the painful feeling of defeat is also hyperactive. This may account for the emotional numbing, inability to feel which accompanies stress.

When individuals playing video games suffer repeated stress and frustration irregularities and abnormalities in all three of these brain systems occur. According to the National Center for Post Traumatic Stress Disorder at Yale University, if two rats are given the same amount of shock and one them can press a lever to stop it, the rat that can do nothing to escape the pain will display brain changes. In the process of playing a video game a player unable to do anything to reach the next level or to stop the trauma of defeat is more likely not to achieve the next level. This is in line with experimental studies in animals which have shown that being able to escape, i.e., to control their escape of stress means that certain brain changes do not occur. This also holds true for humans.

When a person plays a video game and fails at a particular level for a repeated period of time the hypothalamus secretes CRF and the pituitary gland adjusts by lowering its number of CFR receptors, i.e., alpha 2 receptors. However, other CRF reaches other areas of the brain which are also sensitive to CRF. These other areas are not capable of lowering their number of receptors as readily as can the pituitary gland.

Excess release of CRF from the brain hypothalamus to these other brain centers is compensated by additional alpha 2 receptors when it is exhibited to the game player that there is an escape from the level achieved and this information is stored in the brain's memory bank. As part of the novel invention this exhibition occurs in the form of a video tape showing all levels of video play to the final level of the game. Thus, because the player understands that there is an escape from the level of play achieved by him excess release of the CRF from the hypothalamus is absorbed by additional alpha 2 receptors which are made available due to diminished stress. Too much CRF is produced when no escape is known. This makes a player overreact and prevents him from achieving a higher level of play. The player remembers the last time he was defeated at a particular level and exhibits an inability to go beyond to a new level of play.

It is recognized now in the human that under stress, as brain cells secrete norepinepharine, alpha 2 receptors sense this and slow down the accumulation. The inventor theorizes that in players who have played video games for a particular period of time and have been defeated on numerous occasions the number of alpha 2 receptors is significantly lower than in players who know of an escape mechanism to enable them to reach a higher level of play. A subliminal auditory message also is helpful.

The current invention utilizes as a novel element a video tape which contains a specific game played in its entirety. The inventor has discovered that watching a game played in its entirety enhances a player's playing ability significantly by reducing the stress associated with a specific mental state, namely, the perception that it is impossible to play the game through to its highest level of play. The tape contains a video game played from beginning to end by an advanced player or computer showing the actual play on a video screen. The inventor discovered that, for example, after spending many hours playing a single Nintendo TM video game, the player develops a certain stress level and a certain anticipation of failure even if a new level is achieved beyond that never attained previously. Generally the new player or the player who achieves the new level has no idea of what to expect at the new level and frustration and significant stress results.

These types of video games contain complex puzzle-like aspects and while they are attractive for the player they are also a source of stress which helps to defeat the player. Research performed by the inventor indicates that a player can significantly and unexpectedly increase his efficiency by watching the video game played through all levels of play. By having the player experience prior viewing of the video game through all levels of play it shows methods of where to go: how to find hidden items, and how to acquire necessary fighting techniques and tactics to escape destruction. The novel method produces much more motivation to play and succeed and eliminates significant stress associated with prior constant defeat and presents help to the player to form a plan of action.

Although the novel learning technique is directed to a Nintendo TM game system, it is applicable not only to Nintendo TM but to other home video game systems. In particular, any one player game system played on a television set is included. The novel learning system presented here is limited to a video game cassette comprising a player adventure type game in which a player is pitted against mazes and enemies in an attempt to reach an ultimate level, or destination to complete the game.

The levels get progressively more difficult in the game. Accordingly, heretofore most players reached a particular point in a game and found it virtually impossible to surpass that level in part due to stresses associated with not being able to develop a plan of action and strategy at the other levels and not knowing what to do. The stresses associated with playing the game often defeat the player.

Examples of games in the Nintendo TM game system for application of this invention are: BLASTER MASTER TM, ZELDA TM, LINK TM, GUARDIAN LEGEND TM, METROID TM, and LIFE FORCE TM, to name a few. The concept and novel learning system presented here is not for use on two player games in which the players are pitted against each other or a computer. Examples of such games include sports games such as baseball, boxing, tennis, football, racing, and target shooting.

The inventor has been able to determine from evaluations that players achieve a higher degree of enjoyment from these games and a higher degree of satisfaction, and stress alleviation when they improve their ability to play the game and achieve a higher level of play and when they know that this is actually probable.

It is important to understand that the Nitendo TM invention games, although difficult, have been mastered by a number of human players as well as computers. A countless variety of games exist with many variations of difficulty among them. The inventor has determined that most players do not possess the skill necessary to achieve all levels of play without some type of intervention. The inventor has likewise determined that utilizing this method as a learning tool the players achieve the necessary skill to play at the higher levels of a particular game even though they are initially bewildered by the complexity of the game. The inventor has determined that players are easily frustrated when they are unable to devise a strategy to achieve the higher levels of play.

Very few people without utilizing the novel learning system can complete any of the adventure games. Moreover, without this learning system it requires an extremely long time to attain the eye-hand coordination necessary to complete a one player adventure game. Many players get to a certain point or level in the games and find themselves unable to advance. Investigation by the inventor has revealed that significant numbers of players progressively achieve significantly higher level of play after utilizing the novel method of the invention.

OBJECTS OF THE INVENTION

It is an object of the invention to provide a method for improving one's skill for playing a particular video game.

It is an object of the invention to provide a method for improving one's skill for playing a video game by a video display of the successful play necessary for improved play.

It is another object of the invention to improve one's skill for playing a video game by illustrating a solution thereby diminishing the negative psychological effect of stress caused by inability to conceive a way to escape the threat posed in the game.

Thus, it is yet another object of this novel invention to provide a learning system that will present a plan of action to an action game player for achievement of higher levels of play than previously achieved.

Another object of the novel invention is to eliminate and reduce the stress associated with the play of adventure type video games which contributes to the lack of success in achieving higher levels of play.

Yet another object of the invention is to motivate players of one player adventure games by teaching a plan of action which will enable them to achieve higher levels of play.

SUMMARY OF THE INVENTION

The object and general purpose of this novel invention are accomplished by providing a player of one player action type adventure games with a plan of action whereby the player is shown that the play of the game through all levels of play is achievable. The player is taught by means of feedback indicating increasingly higher levels of play achievement as compared with previous levels. The novel method does this by diminishing the effects of stress associated with playing the game and not knowing a solution to achieve a higher level of play. Thus, the player is taught escape methods and techniques to higher levels are achievable and thereby the negative brain processes which are put into play during stress while engaged in a game are controlled. The number of alpha 2 receptors necessary to slow down the accumulation of CRF is increased by presenting an escape mechanism.

BRIEF DESCRIPTION OF THE DRAWINGS

Other objects and many of the intended advantages of the invention will be appreciated as same become understood by reference to the following detailed description and when considered in conjunction with the accompanying drawings in which like reference numerals designate like parts throughout the figures thereof, to wit.

DESCRIPTION OF THE PREFERRED EMBODIMENT

Figure 1:
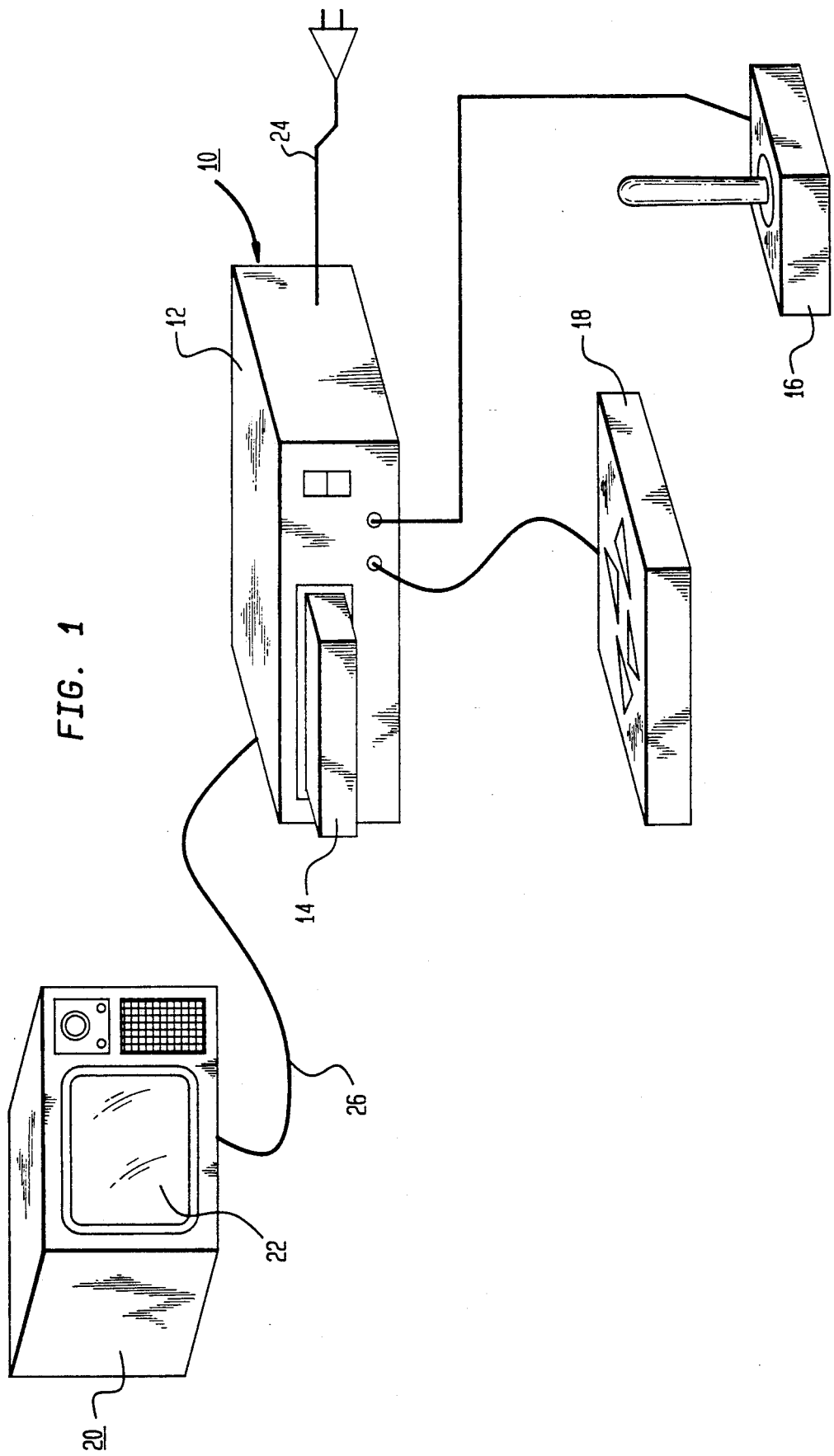
FIG. 1 is a display of a video game module, a video game cartridge, and a video monitor.

Referring first to FIG. 1 a interactive video game playback system such as for example, Nintendo TM, is shown generally at 10. Video images derived from a video recording medium, for example a Nintendo TM cartridge, using a game display unit 12 are displayed on a screen of a television simultaneously with the video images generated from microprocessor controlled game cartridge 14. The video game display unit 12 permits a user (not shown) to manually control the position of a generated video image displayed by either a joy stick control unit 16 or a button control unit 18. Information is used in such a manner that the video images from the game display unit 12 interact with movements of video images controlled by the joy stick control unit 16. Such a system is described in detail in U.S. Pat. No. 4,359,223 issued in 1982 to Baer, et al.

The video cartridge 14 is a one player adventure type game, such as for example, Blaster Master TM, Zelda TM, Link TM, Guardian Legend TM, Metroid TM or Life Force TM as marketed by Nintendo TM. The game cartridge 14 is such that a player is pitted against mazes and enemies in an attempt to reach an ultimate level, or destination to complete the game. The output of the game cartridge 14 interpreted by the game display unit 12 is fed into a television monitor 20 and displayed on a screen 22 thereof.

The game display unit 12 has power supplied thereto by means of a power cord 24. The game display unit 12, for example, a Nintendo TM player with a cartridge 14, for example, a Nintendo TM cartridge, is connecte via cables 26 to the appropriate input terminals (for example, the antenna terminals) of the television monitor 20.

Figure 2:
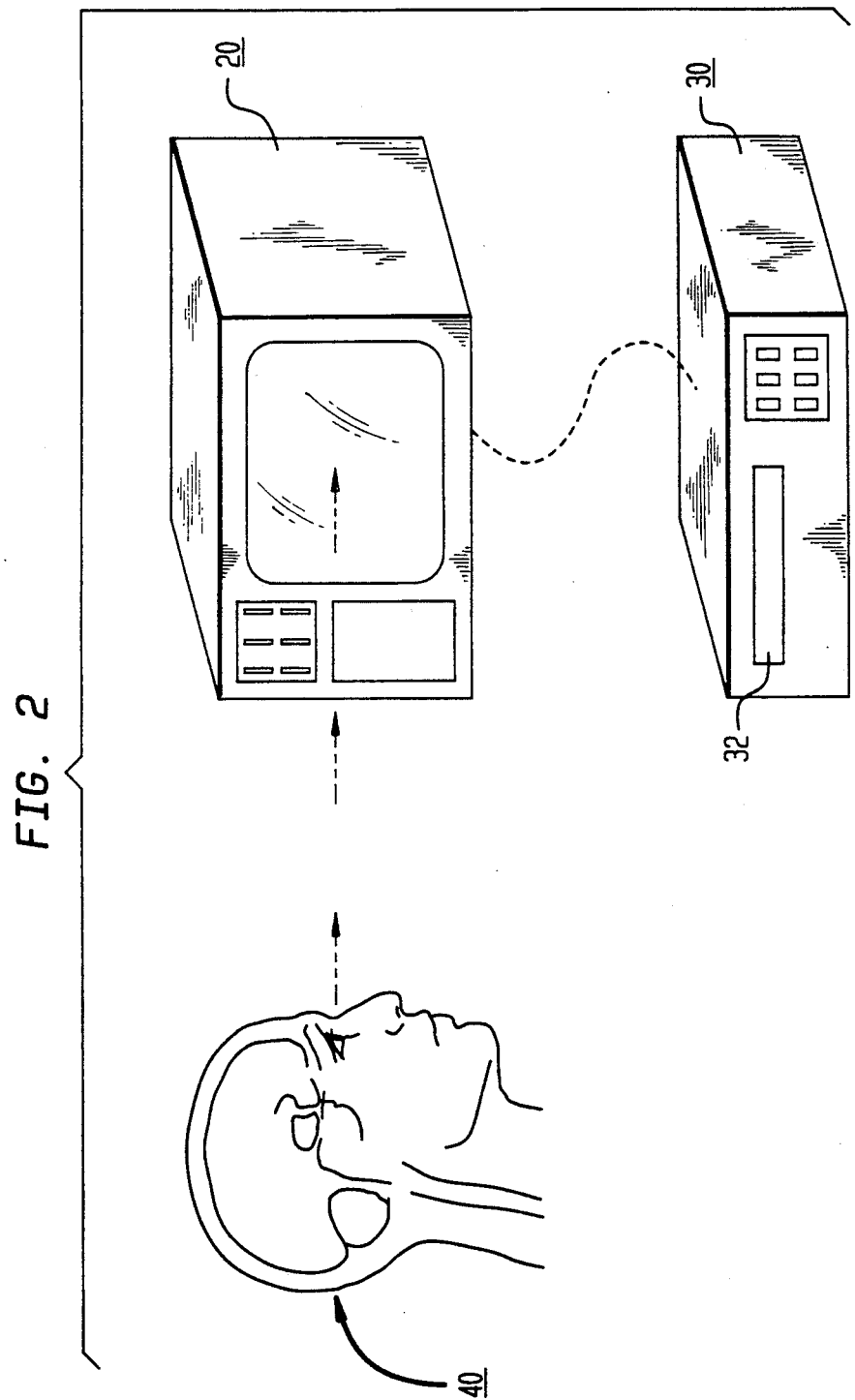
FIG. 2 is a display of a player observing a video monitor playing a video tape.

In FIG. 2 there is shown a television monitor 20 connected to a video tape player 30. Shown inserted is a video tape 32. Video tape 32 contains a complete video recording of all levels of play for the game displayed by the cartridge 14 shown in FIG. 1. As the video game produced by the cartridge 14 is played on the television monitor 20 it is recorded by the video tape player 30 as a skilled person or machine plays the Nintendo TM game 14 through all levels of play available. Tape 32 is shown being played from the monitor 20 and observed by player 40.

Before observing the video game shown by the video game cartridge 14 played through all levels of play on the monitor 20, the player 40 first plays the video game 14 on the cartridge as it is displayed on the monitor 20, interacting with the game, via either the unit 16 or the button control unit 18. The player 40 plays the highest level of play his skill allows. Thereafter according to the method of the invention the player 40 then observes the video game 14 as recorded on the video tape 32 played through all levels of play on the television monitor 20. Immediately thereafter the player 40 again plays the video game 14 until he loses or until he plays through all levels of play. It is optional whether the player 40 records the level of play achieved, for example, level I, level II, level III, level IV, etc. If so, the player 40 then records and compares the levels of play achieved, after observation of all levels of play on the video tape, to the level previously achieved prior to the observation.

Figure 3:
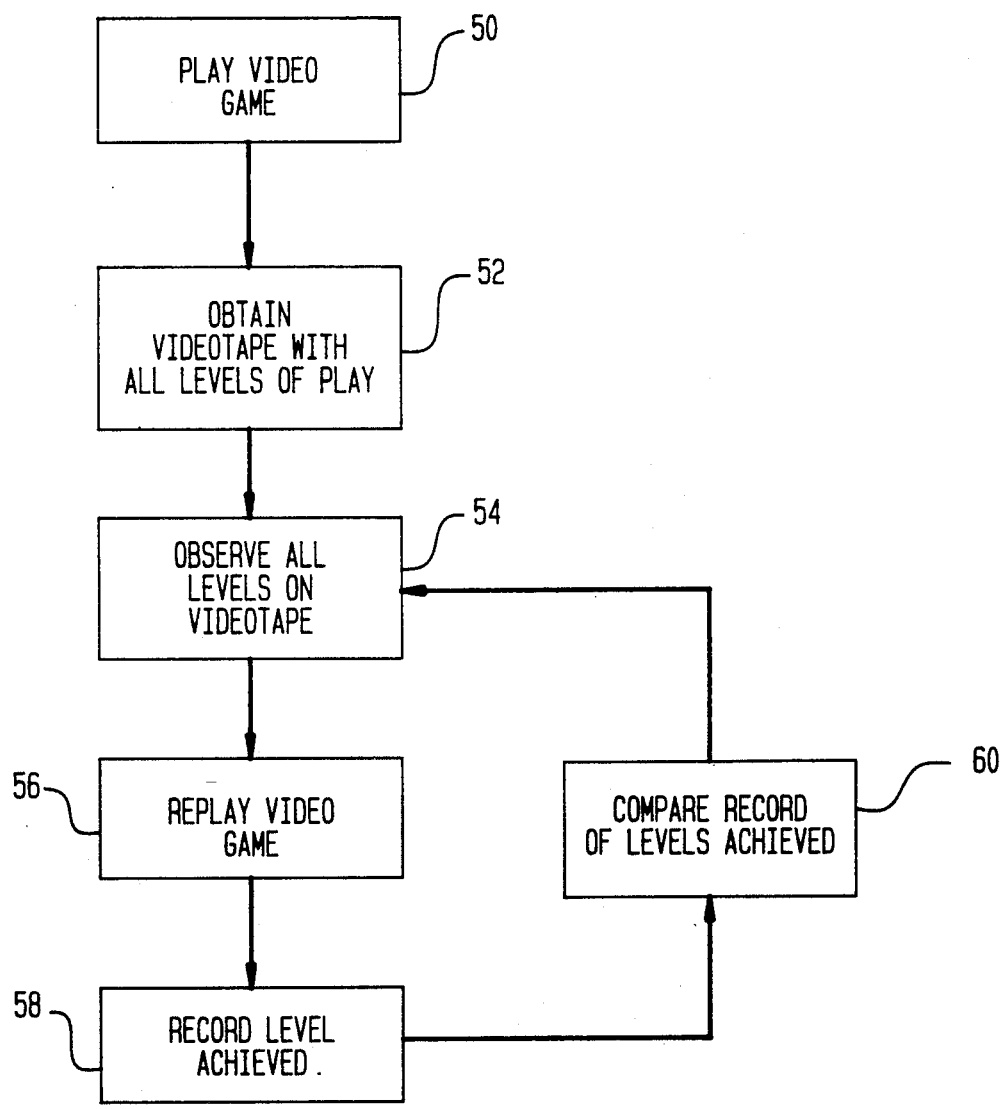
FIG. 3 is a flow chart illustrating the novel training method.

In FIG. 3 there is illustrated in block form the novel method of the invention. To execute the method the player 40 first plays the video game on the video cartridge 14 as shown in block 50. Next the player 40 obtains a video tape with all levels of play for the video game cartridge 14 recorded thereon. This is illustrated in the block 52. Next the player 40 plays the video tape, tape 32 for example, as shown in FIG. 2. The player 40 observes all levels of play as shown on the video tape 32 on the television monitor 20. This step is illustrated in block 54. Next, the player 40 repeats the step shown in block 50, replays the video game on the cartridge 14 as illustrated in block 56. Upon completion by the player 40 of a replay of the video game on the cartridge 14, the player records the level of play achieved, e.g., memorializing it as by writing it down, or alternatively by making a video tape of the play. This is illustrated in block form as 58 in FIG. 3. The player 40 next compares the recorded level of play for the video game cartridge 14 achieved to a record indicating any previous levels of play, for example, level II, level III, or level IV. This comparison is illustrated in block 60.

In the method, player 40 next again observes all levels of play on the video tape 32 a second time and then repeats the steps shown in blocks 56 and 58 and 60. The player continues this process through as many cycles as is convenient in a specified period of time, for example, two hours.

It will be understood that the foregoing disclosure is intended to be merely exemplary and not to limit the scope of the invention which is to be determined solely by reference to the amended claims.

What is claimed is:

1. A method for increasing a skill level of a first player of an interactive one player adventure video game towards a higher skill level exhibited by a second player comprising the steps of:
   (a) Said first player obtaining a continuous video recording of said interactive one player adventure video game played by a second player who is constantly threatened by destruction during the game through all available levels of play for said interactive one player adventure video game; then
   (b) Displaying to said first player the continuous video recording on a video recording player said continuous recording of the interactive one player adventure video game played by said second player who is constantly threatened during a game through all available levels of play for said interactive one player adventure video game; the
   (c) Said first player passively observing on a video monitor the video game being played through all levels of play by said second player;
   (d) Thereafter said first player being constantly threatened during the game with destruction and playing said interactive video game until destruction occurs at a level of play;
   (e) Said first player again passively observing the interactive one player adventure video game being played by said second player through at least the next higher level of play; whereby said first player's level of skill for playing said interactive one player adventure video game increases insignificantly towards the level of skill exhibited by said second player.

2. A method for increasing a skill level of a first player playing an interactive video game comprising the steps of:
   (a) Said first player being constantly threatened with destruction during the game and playing the video game until destruction of said first player occurs on a video screen;
   (b) Said first player obtaining a continuous video recording of a second player of the video game wherein said second player plays through all available levels of play for said game without being destroyed on the screen; then,
   (c) Said first player simultaneously playing and observing the video recording of said second player on a video recording player wherein said video game is shown being played by said second player through all available levels of play for said video game;
   (d) Simultaneously playing a recording of a subliminal audio description of actions of the second player appearing on the screen and each action taken by the second player to avoid destruction on the screen during the video recording;
   (e) During said simultaneous playing and observing step, said first player passively observing the second player of said game playing through all levels of play and listening by said first player to the subliminal audio description; then
   (f) Said first player thereafter playing said video game until destruction of said first player on the screen occurs and then;
   (g) Said first player again passively observing the recording of the second player of the game played through a level of play beyond where said last said destruction occurred; whereby said first player's level of skill for playing said game increases significantly.

* * * * *